(12) United States Patent
Brower

(10) Patent No.: US 8,883,181 B2
(45) Date of Patent: *Nov. 11, 2014

(54) COMPOSITIONS FOR TREATING PLANT PATHOGENS

(71) Applicant: William Brower, Fortville, IN (US)

(72) Inventor: William Brower, Fortville, IN (US)

(73) Assignee: William Brower, Fortville, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/089,799

(22) Filed: Nov. 26, 2013

(65) Prior Publication Data

US 2014/0079669 A1    Mar. 20, 2014

Related U.S. Application Data

(60) Division of application No. 13/048,047, filed on Mar. 15, 2011, now Pat. No. 8,591,926, which is a continuation-in-part of application No. 11/622,629, filed on Jan. 12, 2007, now Pat. No. 7,906,131, which is a continuation of application No. PCT/US2005/025012, filed on Jul. 13, 2005.

(60) Provisional application No. 60/587,563, filed on Jul. 13, 2004.

(51) Int. Cl.
*A01N 25/00*    (2006.01)

(52) U.S. Cl.
USPC .......................................................... 424/405

(58) Field of Classification Search
USPC ................................ 424/405, 93.4, 93.51, 725
See application file for complete search history.

(56) References Cited

U.S. PATENT DOCUMENTS

| | | | |
|---|---|---|---|
| 4,975,105 A | 12/1990 | Kremer et al. | |
| 5,288,488 A | 2/1994 | Backman et al. | |
| 5,639,794 A | 6/1997 | Emerson et al. | |
| 6,228,265 B1* | 5/2001 | Henderson | 210/610 |
| 6,280,719 B1* | 8/2001 | Suh | 424/93.43 |
| 6,471,741 B1 | 10/2002 | Reinbergen | |
| 6,602,500 B1 | 8/2003 | Kharbanda et al. | |
| 6,649,566 B2 | 11/2003 | Doostdar | |
| 7,485,110 B2* | 2/2009 | Koenig et al. | 604/289 |
| 7,906,131 B2* | 3/2011 | Brower | 424/405 |
| 8,591,926 B2* | 11/2013 | Brower | 424/405 |
| 2002/0174697 A1* | 11/2002 | Reid et al. | 71/23 |
| 2003/0068303 A1 | 4/2003 | Selvig et al. | |
| 2003/0082792 A1 | 5/2003 | Bergstrom et al. | |
| 2007/0110725 A1 | 5/2007 | Brower | |
| 2012/0090365 A1* | 4/2012 | Ersek et al. | 71/7 |

FOREIGN PATENT DOCUMENTS

| | | |
|---|---|---|
| DE | 197 39 364 A1 | 4/1998 |
| EP | 1 241 247 A1 | 9/2002 |
| WO | WO 94/19950 A1 | 9/1994 |
| WO | WO 99/05257 A1 | 2/1999 |
| WO | WO 00/36085 A1 | 6/2000 |
| WO | WO 00/64837 A1 | 11/2000 |
| WO | WO 01/52869 A1 | 7/2001 |
| WO | WO 00/51435 A1 | 9/2002 |
| WO | WO 02/091824 A2 | 11/2002 |
| WO | WO 2004/002227 A1 | 1/2004 |
| WO | WO 2006/017361 A1 | 2/2006 |

OTHER PUBLICATIONS

"Fertiliser prodn—involves culturing leguminous, photosynthetic and sulphur bacterial and mixing with cultured nitrifying, cellulose decomposing etc. bacteria", WPI/Thomson, vol. 1985, No. 12, Feb. 12, 1985.
Ban S et al., "Prevention of soil disease in plants—comprises using root fungi of VA fungi and resistant fungi", WPI/Thomson, vol. 1993, No. 37, Jul. 2, 1993.
English Translation of DE 197 39 364 A1, Apr. 30, 1992.
European Search Report dated Jul. 9, 2012 in European Patent Application No. 12159613.4, pp. 1-14.
Kitamura et al., "Soil phytopathogenic antifungal organic compsn.—contg. mixt. of photo-synthetic bacteria and plant extract residue and/or drainage waste sludge", WPI/Thomson, vol. 1988, No. 25, May 12, 1988.
Miura, T., "Microbial antagonists—are fermentative mixtures comprising organic substances of animal and plant origin, organic mud, nutrients and microorganisms", WPI/Thomson, vol. 1990, No. 19, Mar. 30, 1990.

* cited by examiner

*Primary Examiner* — Ralph Gitomer
(74) *Attorney, Agent, or Firm* — Woodard, Emhardt, Moriarty, McNett & Henry LLP

(57) ABSTRACT

The present invention provides formulations and methods for preventing, suppressing, treating, or controlling pre- or post-harvest disease or decay in plants. In the inventive method, plants are contacted with a formulation including an antagonistic microorganism and a booster composition. The booster composition generally includes about 3 parts Kaolin clay, about 1 part yeast, about 1 part *Yucca* plant extract, and about 1 part calcium-source material. The antagonistic microorganism may be included in an amount of between about 0.02 parts and about 0.5 parts by weight of the formulation, with about 0.04 parts antagonistic microorganism being preferred in testing to date. The formulation is typically applied to the above ground structures of the plant, including its leaves, flowers, stems, trunk, blossoms and fruit.

15 Claims, 1 Drawing Sheet

COMPOSITIONS FOR TREATING PLANT PATHOGENS

CROSS REFERENCE TO RELATED APPLICATIONS

This application is a division of U.S. patent application Ser. No. 13/048,047, filed Mar. 15, 2011 now U.S. Pat. No. 8,591,926, which is a continuation in part of U.S. patent application Ser. No. 11/622,629, filed Jan. 12, 2007 (now U.S. Pat. No. 7,906,131), which is a continuation of International Patent Application Serial No. PCT/US2005/025012, filed Jul. 13, 2005, which claims the benefit of U.S. Provisional Patent Application Ser. No. 60/587,563, filed Jul. 13, 2004. The entire contents of each application identified in this Cross Reference to Related Applications is hereby incorporated herein by reference.

FIELD OF THE INVENTION

The present invention relates generally to formulations and methods for controlling and suppressing plant pathogens, and more particularly to formulations and methods for controlling and suppressing plant pathogens with a "booster" that enhances the activity of antagonistic microorganisms such as bacteria and yeasts.

BACKGROUND OF THE INVENTION

Plants including many commercially valuable cultivars ranging from fruit trees and crop plants to ornamental shrubs are affected by a wide variety of microorganisms, including bacterial and fungal pathogens. These pathogenic microorganisms cause great damage, and a great deal of time and expense is devoted to trying to protect plants from these pathogens and/or to minimize the damage they do once they infect a plant.

Applicant's prior work has developed antagonistic microorganisms including mixtures of bacteria and/or fungi that may be used to fight and/or treat pathogenic microorganisms. A more universal approach is desired though, and particularly an approach that improves the efficacy of a broad range of antagonistic bacteria and/or fungi. Of particular interest would be a formulation that improves the performance of antagonistic bacteria and/or fungi under either pre-harvest or post-harvest conditions.

A need therefore exists for formulations that may be used to improve the performance of a wide variety of antagonistic bacteria and/or fungi under either pre-harvest or post-harvest conditions. The present invention addresses that need.

SUMMARY

Briefly describing one aspect of the present invention, there is provided a "booster" formulation for enhancing the activity of an antagostic microorganism. The booster formulation preferably comprises kaolin clay, a calcium salt, yeast extract, and *Yucca* plant extract. The four components are preferably provided in a ratio of about 3:1:1:1 by weight.

The booster formulations may be used in conjunction with one or more antagonistic microorganisms. In one preferred embodiment the antagonistic microorganism may comprise an antagonistic yeast. In another preferred embodiment the antagonistic microorganism may comprise an antagonistic bacteria.

Another aspect of the present invention is a method for improving the ability of an antagonistic microorganism to control plant pathogens. The inventive method comprises contacting a plant with a formulation comprising an antagonistic microorganism and a booster composition, with the booster composition comprising: a) about 3 parts kaolin clay; b) about 1 part yeast extract; c) about 1 part *Yucca* plant extract; and d) about 1 part calcium-source material.

Another aspect of the present invention provides a method for improving the ability of an antagonistic microorganism to control plant pathogens by contacting the plant with a formulation comprising an antagonistic microorganism and a booster composition, with the booster composition comprising: a) about 3 parts kaolin clay; b) about 1 part yeast extract; c) about 1 part *Yucca* plant extract; d) about 1 part calcium-source material; and e) between about 0.02 parts and about 0.5 parts antagonistic microorganisms, by weight.

In another aspect of the present invention the formulation is dispersed in an aqueous preparation and includes between 1.5 and 10 pounds of kaolin clay per 100 gallons of aqueous preparation.

In another aspect of the present invention the calcium source material comprises a calcium salt, which may be calcium glucoheptonate, calcium chloride, calcium sulfate, or calcium carbonate, and is preferably calcium glucoheptonate In another aspect of the present invention the antagostic microorganism comprises one or more beneficial bacteria, which may be selected from the group consisting of: *Bacillus subtilis*, *Baccillus licheniformis*, *Bacillus axotoformans*, *Bacillus megaterium*, *Bacillus coagulans*, *Bacillus pumulis*, *Bacillus thurengiensis*, *Bacillus stearotermophilis*, *Paenbacillius polymyxa*, *Paenibaccillus durum*, *Azotobactor chroococcum*, *Pseudomonas aureofaceans*, and *Pseudomonas fluorescence*.

In another aspect of the present invention the antagonistic microorganism comprises one or more beneficial fungi, which may comprise *Monilinia fructicola*.

In another aspect of the present invention the antagonistic microorganism include one or more beneficial yeasts, which may be elected from the group consisting of: *Candida* spp; *Cryptococcus* spp; *Pichia* spp; *Debaryomyces* spp; *Bulleromyces* spp; *Sporobolomyces* spp; *Rhodotorula* spp; *Aureobasidium* spp; *Issatchenkia* spp; *Zygosaccharomyces* spp; *Dekkera* spp; and *Hansenula* spp., and preferably comprises *Candida saitoana*.

The method of applying the formulation may be selected from the group consisting of, spraying, dusting, and drenching said plant with said formulation.

DETAILED DESCRIPTION OF THE INVENTION

Figure 1:
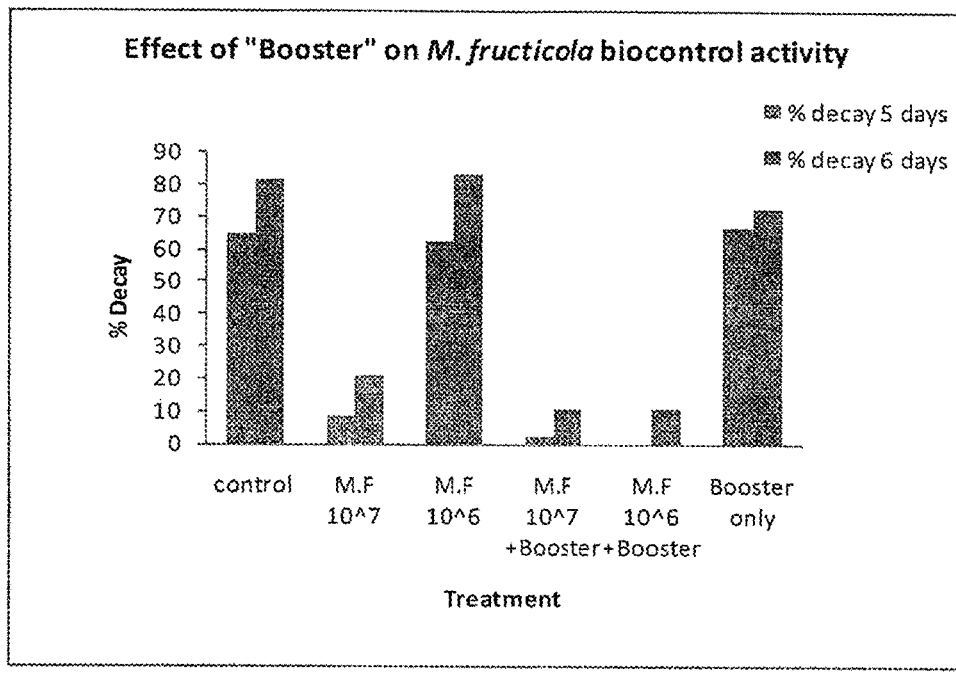
FIG. 1 is a table showing the effect of "Booster" on *M. fructicola* biocontrol activity.

For the purposes of promoting an understanding of the principles of the invention, reference will now be made to certain embodiments and specific language will be used to describe the same. It will nevertheless be understood that no limitation of the scope of the invention is thereby intended. Any alterations and further modifications in the described processes, systems or devices, and any further applications of the principles of the invention as described herein, are contemplated as would normally occur to one skilled in the art to which the invention relates.

Before discussing the details of certain aspects of the formulations and methods of the present invention, certain terms used in the description and claims will be described. As used herein, antagonistic microorganisms are microorganisms that work to prevent, suppress, treat or control pre- or post-harvest disease or decay in plants, including their fruits and/or harvestable parts. For example, the antagonistic microorganism may work to prevent, suppress, treat or control a pre-harvest disease state, such as a blight. Similarly, the antagonistic microorganisms may work to prevent, suppress, treat or control post-harvest decay, such as rot.

The antagonistic microorganism(s) may comprise a bacterium, a fungus, or something else. The antagonistic microorganism may be antagonistic to a plant pathogen which may itself be a bacterium, a fungus, or something else.

Suppression or suppressing generally refers to preventing a disease or pathogen from infecting or affecting a given plant or group of plants. When these terms are used herein no claim is made as to the actual mechanism of suppression, for example, a given suppressor may be acting as a biocide, bactericide, bacteriostat, fungicide, fungistat, insecticide, or it may interfere with one or more functions of a given pathogen that enables the pathogen to infect a given plant under a given set of environmental conditions, or by any other mechanism. All that is to be inferred by use of the terms suppression or suppressing is that a given formulation appears to prevent a plant from becoming symptomatic for infection or assault by at least one plant pathogen.

Similarly, control or controlling generally refers to limiting the economic damage done to a given plant or group of plants by limiting the damage done to the plants by at least one plant pathogen. When this term is used herein no claim is made as to the actual mechanism of pathogen control, for example, a given formulation may act to control a pathogen by acting as a bactericide, bacteriostat, fungicide, fungistat, insecticide, or by interfering with one or more functions of a given pathogen that enables the pathogen to infect a given plant under a given set of environmental conditions, or by any other mechanism. All that is to be inferred by use of the terms control or controlling is that a given formulation appears to reduce the amount of damage done by a plant pathogen to a given plant relative to a similarly situated plant that is likewise infected with the pathogen, but not exposed to the formulation.

The present invention provides methods and formulations for controlling or suppressing plant pathogens including, but not necessarily limited to, pathogenic bacteria and fungi. The group of plant pathogens that can be controlled using formulations made in accordance with various embodiments include, but are not limited to *Erwinia amylovora* the bacteria, which causes fire blight and the fungus *Venturia inaequalis*, which causes Apple Scab.

1. The Booster Formulation.

The present invention provides a formulation that promotes or "boosts" the performance of an antagonistic microorganism. The booster formulation preferably includes kaolin clay, yeast extract, *Yucca* plant extract, and a calcium-source material. The individual components, and their preferred amounts, are discussed in more detail below.

a) Kaolin Clay.

The formulations of the present invention include significant amounts of kaolin clay. As is known to the art, kaolin is a naturally-occurring clay resulting from the weathering of aluminous minerals such as feldspar with kaolinite ($Al_2Si_2O_5(OH)_4$) as its principal constituent. It is a soft, earthy, usually white mineral, that is "generally regarded as safe" by the U.S. Food and Drug Administration.

In the formulations of the present invention the kaolin clay may be provided as a wettable powder that is processed to a very fine particle size, such as Surround® WP by the Engelhard Corp., Iselin, N.J.

The amount of kaolin clay in the booster formulation may range from about 30% to about 60% of the formulation. More preferably the calcium-source material comprises about 40% to about 60% of the booster formulation, and most preferably comprises about 50% of the booster formulation.

b) Yeast Extract.

The formulations of the present invention preferably include yeast extract. As is known to the art, yeast extract is generally a processed yeast product made by removing the yeast cell walls and extracting the cell contents.

The amount of yeast in the booster formulation may range from about 15% to about 20% of the formulation. Most preferably the yeast comprises about 1/6 of the booster formulation.

c) *Yucca* Plant Extract.

The formulations of the present invention also include a yucca plant extract, which is preferably a soluble yucca plant extract derived from the *Yucca schidigera*.

The amount of yucca plant extract in the booster formulation may range from about 15% to about 20% of the formulation. Most preferably the yucca plant extract comprises about 1/6 of the booster formulation.

d) Calcium-Source Material.

The formulations of the present invention also include a calcium-source material. In the preferred formulations the calcium-source material is a calcium salt, and is most preferably calcium carbonate, calcium chloride, calcium sulfate, or calcium glucoheptonate. Calcium glucoheptonate is the most preferred calcium-source material.

The amount of calcium-source material in the booster formulation may range from about 15% to about 20% of the formulation. Most preferably the calcium-source material comprises about 1/6 of the booster formulation.

e. Relative Amounts.

The inventive booster formulation preferably includes about 3 parts kaolin clay; about 1 part yeast extract; about 1 part *Yucca* plant extract; and about 1 part calcium-source material. In other embodiments the inventive booster formulation includes from about 2 parts to about 4 parts kaolin clay; from about 0.5 parts to about 1.5 parts yeast extract; from about 0.5 parts to about 1.5 parts *Yucca* plant extract; and from about 0.5 parts to about 1.5 parts calcium-source material.

When combined with an antagonistic microorganism the inventive formulation preferably includes about 3 parts kaolin clay, about 1 part yeast extract, about 1 part calcium-source material, about 1 part *Yucca* extract, and about 0.02 parts to 0.5 parts antagonistic microorganisms, by weight. In one preferred embodiment the inventive formulation comprises about 3 parts kaolin clay, about 1 part yeast extract, about 1 part calcium-source material, about 1 part *Yucca* extract, and about 0.04 parts antagonistic microorganisms, by weight.

2. Antagonstic Microorganisms.

The formulations according to various embodiments may include at least one antagonistic microorganism. In the most preferred embodiments, the antagonistic microorganism may comprise one or more bacteria or one or more fungi.

a) Beneficial Bacteria.

In one embodiment, the antagonistic microorganism may comprise beneficial bacteria. Beneficial bacteria are bacteria which favorably impact the health of a given plant under a given set of environmental conditions or in response to given realized or potential threat to the health of the plant. Beneficial bacteria may positively impact plant health by a variety of mechanism including, but not limited to: occupying a growth space otherwise occupied by a pathogen; creating a microenvironment which disfavors the colonization, growth or development of at least one plant pathogen; providing at least one compound that is usefully to the health of the plant; providing an increase in the uptake of plant nutrients and minerals; binding to receptors on the surface to the plant that would otherwise be occupied by at least one plant pathogen; directly or indirectly contributing to the well being of other beneficial organisms; and any combination of the aforementioned mechanisms.

Examples of beneficial bacteria include, but are not limited to *Azotobacter chroococcum, Azobacter polymyxa, Azobacter vinleandii, Bacillus amyloliquefaciens, Bacillus azotoformans, Bacillus coagulans, Bacillus fluorescens, Baccillus licheniformis, Bacillus megaterium, Bacillus polymyxa, Bacillus pumilis, Bacillus sterotermophilis, Bacillus subtilis, Bacillus thuringiensis, Deinococcus erythromyxa, Paenibacillus azotofixans, Paenibacillus durum, Paenibaccillus gordonae, Paenbacillius polymyxa, Pseudomonas aureofaceans, Pseudomonas fluorescens, Pseudomonas monteilii, Streptomyces griseoviridis, Streptomyces lydicus*, and mixtures thereof.

In one embodiment the antagonistic microorganism comprises a mixture of bacteria from the group consisting of: *Azotobacter chroococcum, Azobacter polymyxa, Bacillus amyloliquafacians, Bacillus azotofomrans, Bacillus coagulans, Baccillus licheniformis, Bacillus megaterium, Bacillus pumulis, Bacillus stearothermophilis, Bacillus subtilus, Bacillus thurengiensis, Deinococcus erythromyxa, Paenibaccillus durum, Paenibaccillus gordonae, Paenbacillius polymyxa, Pseudomonas aureofaceans*, and *Pseudomonas fluorescence*, and mixtures thereof. The mixture of bacteria is preferably included in the formulation in the following amount: about 3 parts Kaolin clay, about 1 part yeast extract, about 1 part calcium-source material, about 1 part *Yucca* extract, and about 0.04 parts bacteria mixture, by weight.

In another embodiment the antagonistic microorganism comprises *Bacillus pumilus, Bacillus lichenformis, Bacillus subtilis, bacillus amyloliquefaciens* and *Bacillus fluorescens (putida)*.

b) Beneficial Fungi.

The formulations according to various embodiments may include at least one beneficial fungal species. Beneficial fungi are fungi which favorably impact the health of a given plant under a given set of environmental conditions or in response to given realized or potential threat to plant health. Beneficial fungi, positively impact plant health by a variety of mechanism including, but not limited to: occupying a growth space otherwise occupied by a potential pathogen; creating a microenvironment which disfavors the colonization, growth or development of at least one plant pathogen; providing at least one compound that is usefully to the health of the plant; providing an increase in the uptake of plant nutrients and minerals; binding to receptors on the surface to the plant that would otherwise be occupied by at least one plant pathogen; directly or indirectly contributing to the well being of other beneficial organisms; and any combination of the aforementioned mechanisms.

Examples of beneficial fungi include, but are not limited to *Laccaria bicolor, Laccaria butilus, Laccaria laccata, Paenibacillus polymyxa, Paenibacillus durum, Pisolitus tinctorius, Rhizopongon ellanae, Rhizopogon rubescens, Rhizopogon subscaerlescens, Rhzopogon vulgaris, Scleroderma cepa* and *S. citrinum*.

The antagonistic microorganism may be a yeast. For example, the antagonistic microorganism may comprise one or more beneficial yeasts selected from the group consisting of: *Candida* spp; *Cryptococcus* spp; *Pichia* spp; *Debaryomyces* spp; *Bulleromyces* spp; *Sporobolomyces* spp; *Rhodotorula* spp; *Aureobasidium* spp; *Issatchenkia* spp; *Zygosaccharomyces* spp; *Dekkera* spp; and *Hansenula* spp. In other embodiments the antagonistic microorganism may be comprises the yeast *Candida saitoana* and/or the yeast *Saccharomyces cervisiae*.

3. Other Additives.

The formulations according to various embodiments may also include at least one microorganism that is involved in nutrient cycling. Nutrients cycled by a given microorganism may benefit a plant by, for example, directly supply the plant with at least one useful compound, or by supplying other useful microorganisms in the microenvironment with at least one necessary or useful compound. Additional benefits from nutrient recycling may include replenishing at least one compound that adversely affects the health or survival of at least one plant pathogen. It is to be understood that a given microorganisms may simultaneously perform more than one of the aforementioned functions in a given microenvironment.

The formulations according to various embodiments may include a carbon source such as simple or complex carbohydrates, and/or a nitrogen source such as ammonia. Phosphates, such as potash, may also be included.

The formulations according to various embodiments may also include an additional component to act as a sticking agent. A sticking agent is a compound that has as at least one its characteristics the ability to adhere to a surface structure of a plant or to at least one other component in a given formulation. Suitable sticking agents include, but are not limited to additional yucca plant extracts, additional clays, and fine wet-able powders. Sticking agent can be included in amounts up to about 12 wt % of the total weight of a ready to use formulation.

The formulations according to various embodiments may also include at least one additional component that helps to protect the components of the formulation from the damaging effects of ultraviolet (UV) radiation, or from rapid desiccation. These compounds include, but are not limited to fine clays, aluminum oxide, zinc oxide, aluminum silicate and the like.

The formulations according to various embodiments may also include at least one wetting agent. A wetting agent promotes the dispersal of the formulation in an aqueous environment. Wetting agents may also promote a more even, more efficient spreading of various components in the formulation onto above ground plant structures including, but not limited to, leaves, stems, petioles, bark, blossoms, fruits and the like.

In one embodiment the formulation can also include a nutrient. Preferably the nutrient is selected for its ability to enhance the stability, longevity and/or propagation of the beneficial bacteria, fungi, plant structure or root plant. Examples of nutrients for use with the present invention includes, but are not limited to humic acids, sugars, dextrins (particularly maltodextrin), dextrose, and dried yeast, or yeast extract. The nutrients can be added in amounts ranging between about 1 wt % and about 15 wt %, based upon the total weight of the formulation.

The formulation can also include one or more emulsifying agents known to those skilled in the art.

The plant pathogen control or suppression formulation can also include a surfactant. Surfactants can be used in the formulation including the anionic, cationic, and/or non-ionic types. Examples of surfactants include but are not limited to: aliphatic sulfonic ester salts like lauryl sulfate, aromatic sulfonic acid salts, salts of lignosulfates, and soaps. Examples of nonionic surfactants are the condensation products of ethylene oxide with fatty alcohols such as oleylalcohol, alkyl phenols, lecithins, and phosphorylated surfactants, such as phosphorylated ethylene oxide/propylene oxide block copolymer and ethoxylated and phosphorylated styryl-substituted phenol. Additional surfactants are anionic wetting agents, such as sodium salts of sulfated alkyl carboxylate, and/or alkyl naphtalenesulphonate, and/or dispersing agents such as naphthalene formaldehyde condensate.

The formulation can also include a variety of other ingredients such as vitamins and minerals. Examples of vitamins for use in the composition include but are not restricted to the following: biotin, folic acid, vitamins A, B, B2, B3, B6, B7, B12, C, D, E, and K, as well as folic acid and/or humic acid.

Minerals that may enhance the growth of the plant and/or promote the performance of the antagonistic microorganism may also be included. Also, one or more metals, such as iron, potassium, sulfur, magnesium, boron, manganese, and zinc, and/or other trace metals, may be included in the inventive formulations and methods.

4. Methods and Timing of Application.

In one embodiment, the method for treating a plant includes a spray or drench application of an aqueous preparations of a formulation for the control or suppression of a plant pathogen to the exposed surfaces of a plant, i.e., any part of the plant extending above ground. This includes the undersides, top, or side surfaces of leaves, stems, trunk bark, buds, blossoms, flowers, fruits and the like, or parts thereof.

Another embodiment includes a spray or drench application about the locus of the plants including, for example, spraying the ground around the plant, particularly from the trunk or stem out to the drip line and/or injecting an aqueous solution of the control formulation into the ground around or under the plants or near the plant roots.

In one embodiment, an application of a formulation for the control or suppression of a plant pathogen can includes dusting the exposed portions of a plant with a solid or powdered composition comprising the formulation. Still another embodiment includes applying the powdered composition to the ground around the plants or in the ground under the plants.

The spraying primarily of a liquid preparation of the formulation can be accomplished by a variety of methods including, but not limited to, blast sprayers, hose reel and hand gun, walking sprays, aerial sprays and the like.

One embodiment provides formulations for the prophylactic treatment of plants prior to exposure to an infectious agent or after confirmed or suspected exposure but before the plant become symptomatic for an infection. Still another embodiment provides control of a pathogen by applying the formation to plants, which exhibit the symptoms and/or other evidence of infection of bacterial or fungal plant pathogens. Still another embodiment can control an infestation of plant pathogen by reducing the amount of damage done to the plant and by at least slowing the rate at which the infestation spreads to other parts of the host plant.

For suppression of a plant pathogen a prophylactic treatment application can be made before the first signs of infestation or when environmental conditions appear to favor an outbreak.

In one embodiment, the inventive formulations are provided as an aqueous ready-to-use spray formulation that is applied prophylactically before the first appearance of flower or in early to full bloom. The prophylactic treatment can be repeated as desired or deemed expedient based upon the environmental conditions and/or the observance of bacterial infestation of neighboring plants, fields or orchards.

In one embodiment, the booster formulations and antagonistic microorganisms of the present invention are used to treat and suppress fire blight. However, when treating for blossom blight, it is preferred not to treat during flower, and instead to treat before flower and/or after flower petal drop, or on stems when new growth is occurring. In one embodiment the treatment is given three to five times, 10 to 14 days apart, for suppression on stems, shoots, trunks and the like. Treatment during flowering may be used for fruit crops such as strawberries.

In one embodiment, the application sequence includes at least a first application to the plants at the early flower stage, including for example, the appearance of first stamen to full bloom. The treatment regime can also include at least one additional application as necessary to control an infection or threat of infection. Appropriate additional applications can be made, for example, at about ⅔ flower or within 7 to 14 days of the first application, or longer depending upon the particular formulation used, environmental conditions and overall health and susceptibility of the plants.

One embodiment provides a formulation for the control or suppression of a pathogen that extends the period of time over which the formulation is effective.

In other embodiments, a control formulation is applied no later then about 2 weeks prior to harvesting edible fruit. In other embodiments the inventive formulation is applied to a plant at harvest to control post-harvest rot.

In one embodiment a formulation for the control or suppression of a pahogen includes at least one beneficial bacteria species. In still another embodiment a given formulation may include, for example, three, four, five, ten, or more different beneficial bacterial species admixed together along with sufficient nutrients. The formulation includes the beneficial bacteria species in an amount sufficient to control or suppress infestation with a bacterial or fungal pathogen in plants. Formulations intended for above ground use, generally include only ecto mycorrhizal species of fungi.

In one embodiment the formulation can includes between about $1.0 \times 10^7$ cfu and about $1.0 \times 10^{11}$ cfu of a single beneficial bacterial species per gal. ($2.5 \times 10^9$ cfu/gal.). In another embodiment the ready-to-use formulation includes between about $1.0 \times 10^8$ cfu and about $1.0 \times 10^{10}$ cfu of a single bacterial species per gal. In another embodiment the antagonistic microorganism is a bacteria that is included in an amount of about $1 \times 10^9$ CFU/g. It will be understood that the ready-to-use formulation can include a number of different bacterial species each included in the above prescribed, approximate amounts.

As with the bacterial species, a given control or suppression formulation can include more than one fungal species, for example, the control formulation may include two, three, four, five or ten or more different species of fungus. The different fungus species can include either endo mycorrhizae or ecto mycorrhizae species, each included fungus species can be included in an amount sufficient to provide at least one beneficial effect to the plant.

In one embodiment, a ready-to-use formulation can contain between about $1.0 \times 10^5$ cfu/gal and about $1.0 \times 10^9$ cfu/gal of a single fungus per gal. ($7.5 \times 10^7$ cfu per gal.). More preferably the ready-to-use formulation can include between about $1.0 \times 10^6$ cfu/gal and about $1.0 \times 10^8$ cfu/gal of a single fungus per gal. It will be understood that the ready-to-use formulation can include a number of different fungi, each included in the above prescribed, preferred amounts.

Still other embodiments includes within its scope the dusting or application of a plant pest control formulation or solid mixture that includes at least one beneficial bacteria, one beneficial fungi, nutrients for the beneficial microorganism, and a fine clay such as Kaolin clay, which may extend the useful half-life of the formulation.

In the powdered mixture various carriers or fillers can be added. Examples of carriers or fillers include, but are not limited to, aluminum silicate, aluminum oxide, attaclay, bentonite, bole, calcium carbonate, calcium sulfate, celite, chalk, diatomaceous earth, dolomite, Fuller's earth, gypsum, Kaolin clay, kieselguhr, lime, limestone, magnesia (powdered), magnesium oxide, pyrophyllite, silica gels, silicates, silicic acid, silicium oxide, and/or talc and mixtures thereof.

One embodiment includes within its scope a concentrated formulation for the control or suppression of a plant pathogen. The concentrated formulation can be either a solid (powdered or granulated) mixture or a concentrated, aqueous mixture. The concentrate can include any or all of the above described ingredients. The concentrated formulation may include the ingredients described in the above in amounts of between about 2 to about 10 fold of the amounts specifically described herein. In use, the concentrate can be admixed with water to provide the ready-to-use formulation.

One embodiment provides a method for treating plants including fruiting plants, ornamental plants and deciduous plants to control and halt the spread of bacterial pathogens including, for example, fire blight (*Erwinia amylovora*). One embodiment includes treating the plants either prophylactically or after observance of infestation of the fire blight bacteria by applying a formulation for the control of the effects of the microorganism.

The application sequence when used as an aqueous formulation for the control of a plant pathogen such as fire blight includes applying a sufficient amount of the formulation to reduce the amount of damage done by the infection relative to plants similarly situated and not treated with the formulation. In one embodiment the ready-to-use spray formulation is applied in an amount sufficient to thoroughly wet or coat the leaves, flowers, stem, bark, trunk and the like without significant run off of the sprayed material. In one embodiment at least one additional application of the formulation may be made as necessary to control the pathogen.

For the purpose of promoting further understanding and appreciation of the present invention and its advantages, the following Examples are provided. It will be understood, however, that these Examples are illustrative and not limiting in any fashion.

Examples 1-7

Multiple field trials were performed to test the efficacy of different formulations of the inventive compositions for plant disease control. Trials were conducted and disease reductions were noted in grape and turf, and yield enhancements were seen in tomato and strawberry, compared to the negative controls. Further trials were conducted and disease reductions were noted in apple, tomato, crabapple, grape, and turf. In total, 10 trials were conducted, and disease reductions relative to the negative controls were noted in 7 trials. Overall, plant disease suppression is generally indicated by the data.

Formulation Descriptions:

All formulations were prepared from Kaolin clay, yeast extract, a calcium source material, *Yucca* extract, and a microbe mix. The microbe mix contained: *Baccillus licheniformis, Bacillus azotofomrans, Bacillus megaterium, Bacillus coagulans, Bacillus pumulis, Bacillus thurengiensis, Bacillus stearothermophilis, Bacillus subtilus, Bacillus amyloliquafacians, Paenbacillius polymyxa, Paenibaccillus gordonae, Paenibaccillus durum, Azobacter polymyxa, Azotobactor chroococcum, Sacchromyces cervisiae, Pseudomonas aureofaceans, Pseudomonas fluorescence, Deinococcus erythromyxa.*

For wettable powders, the components were combined in a ratio of 3:1:1:1:0.04 by weight (components in the order given above). The standard 1× rate was 3.2 to 6.4 g per liter spray, or approximately 12 to 24 g per gallon of spray.

For liquid concentrates (LC), a base mix of Kaolin clay, yeast extract, and a calcium source material was prepared in the ratio of 3:1:1. A 40× liquid concentrate was prepared using 200 g of this base mix and combining that with 40 ml of the soluble portion of a 1:10 suspension of yucca extract (e.g. 50 g per 500 ml of water was prepared and allowed to settle at room temperature for at least 30 minutes), and bringing to a final volume of 1 liter. In some formulations soybean oil was added at a rate of 15 ml per liter of concentrate. The solutions were mixed and sterilized by autoclaving, and allowed to cool to room temperature. To this solution, 16 g of microbe mix per liter were added and mixed to complete the 40× liquid concentrate solution.

All formulations were stored at room temperature prior to analysis.

Test Results:

The following are summary results from the seven field trials of the inventive compositions and methods. The product was formulated with calcium glucoheptonate (BP), calcium chloride (BP1), or calcium carbonate (BP2) as the calcium source material. Trials were conducted using natural disease pressure, except in Grape test 1 where inoculum was introduced into the plots. The trials were conducted by multiple independent investigators, hence the different rating scales. NC indicates the negative control, comprising water or no treatment, depending on the test.

1. Effect on median disease incidence (n=4, 0-100% scale) for black rot on grape.

|    | Fruit infection |
| --- | --- |
| BP | 83 |
| NC | 92 |

2. Effect on median number (n=6 reps) of dollar spot lesions on turf at three different time points.

|    | Jun 26 | Jul 11 | Jul 31 |
| --- | --- | --- | --- |
| BP1 | 21 | 59 | 56 |
| NC | 46 | 48 | 86 |

3. Effect on median disease incidence (n=4, 0-100% scale) of foliar apple scab on fruit trees.

|    | cv. McIntosh | cv. Red Delicious |
| --- | --- | --- |
| BP1 | 66 | 64 |
| NC | 96 | 90 |

4. Effect on median disease rating (n=4 trees, 1-5 scale) of scab on crabapple foliage cv. *Malus* x 'Sutyzam' Sugar Tyme™.

5. Effect on median incidence (n=4 reps; 0-200 scale) of postharvest Botrytis infections on grape pre- and post-incubation under disease conducive storage conditions.

|     | Jun 29 | Jul 22 | Aug 27 |
| --- | --- | --- | --- |
| BP1 | 2.0 | 3.0 | 4.0 |
| NC  | 3.0 | 4.0 | 5.0 |

|     | Pre-incubation | Post-incubation |
| --- | --- | --- |
| BP1 | 0.40 | 1.98 |
| BP2 | 0.03 | 2.83 |
| NC  | 0.50 | 5.98 |

6. Effect on severity of late blight on tomato foliage (n=4 reps; 0-100% scale).

|     | % disease | AUDPC |
| --- | --- | --- |
| BP1 | 79 a | 299 |
| NC  | 99 c | 375 |

7. Effect on median number (n=6 reps) of dollar spot lesions on turf at three different time points.

|     | Jul 13 | Aug 3 | Aug 27 |
| --- | --- | --- | --- |
| BP1 | 21.0 | 46.5 | 108.0 |
| BP2 | 16.5 | 34.0 | 44.0 |
| NC  | 29.0 | 54.5 | 110.0 |

Example 8

The ability of the inventive booster formulation to improve the performance of an antagonistic microorganism was tested using the antagonistic microorganism *Monilinia fructicola*. The test was to see if the inventive booster formulation improves the ability of *M. fructicola* to inhibit post-harvest rotting of citrus.

A booster formulation was prepared according to the following formula (per 500 ml of booster formulation):
  1.18 g Kaolin
  0.39 g $CaCO_3$
  0.39 g Yeast extract
  0.39 g *Yucca*

The booster formulation was applied in 10 μl treatments. After 2 hours, the plants were inoculated with *P. digitatum*. Disease incidence was investigated from 4 days to 6 days. The incidence represented the percentage of fruit displaying rot.

FIG. 1 shows that the inventive booster formulation improves the ability of *M. fructicola* to inhibit post-harvest rotting of citrus.

It can be seen from FIG. 1 that the inventive booster formulation improves the ability of the antagonistic microorganism *Monilinia fructicola* to inhibit post-harvest rotting of citrus. In the replicates using the booster formulation alone, decay at day 5 was approximately 65%, and decay at day 6 was approximately 83%. In the replicates with *Monilinia fructicola* alone, the use of $10^6$ *M. fructicola* did not significantly reduce decay, and the use of $10^7$ *M. fructicola* reduced the incidence of decay to about 10% on day 5 and to slightly more than about 20% on day 6. However, when the booster formulation was used with $10^6$ *M. fructicola*, decay was reduced to about zero on day 5 and to about 10% by day 6. In the replicates using $10^7$ *M. fructicola* with the booster formulation, decay was reduced to less than about 5% on day 5 and to about 10% by day 6. Accordingly, the use of the inventive booster formulation improved the ability of *M. fructicola* to inhibit decay in citrus, and made it possible to use ten times less *M. fructicola* and still obtain good performance.

Example 9

The ability of the inventive booster formulation to improve the performance of an antagonistic microorganism was tested using the antagonistic microorganism *Monilinia fructicola*. The test was to see if the inventive booster formulation improves the ability of *M. fructicola* to inhibit post-harvest rotting of apples.

A booster formulation was prepared according to the following formula (per 500 ml of booster formulation):
  1.18 g Kaolin
  0.39 g $CaCO_3$
  0.39 g Yeast extract
  0.39 g *Yucca*

The booster formulation was applied in 10 μl treatments. After 2 hours, the plants were inoculated with *P. expansum* (10 μl, 1×105 spores/ml). Disease incidence was investigated from 4 days to 6 days. The incidence represented the percentage of fruit displaying rot.

Figure 2:
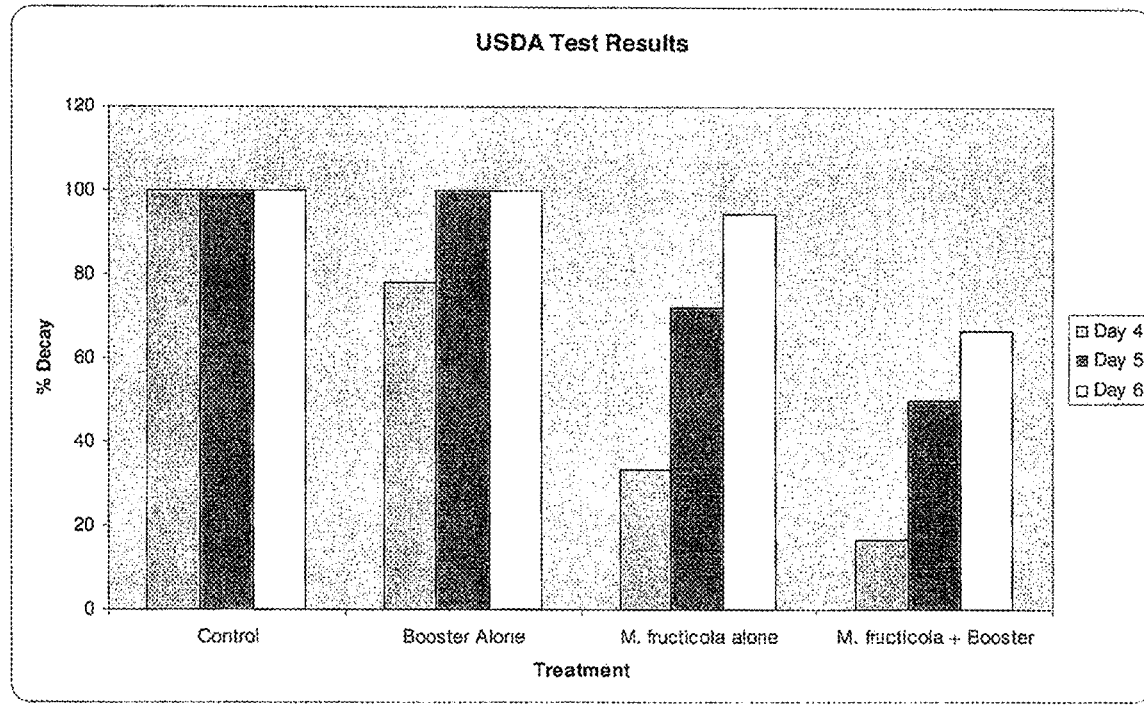
FIG. 2 is a table depicting the USDA test results.

FIG. 2 shows that the inventive booster formulation improves the ability of *M. fructicola* to inhibit post-harvest rotting of apples.

It can be seen from FIG. 2 that the inventive booster formulation improves the ability of the antagonistic microorganism *Monilinia fructicola* to inhibit post-harvest rotting of apples. In the replicates using the booster formulation without *Monilinia fructicola*, there was little affect on rotting at day 4 and no affect on rotting by day 6. In the replicates using *M. fructicola* without the booster formulation, there was some positive affect on rotting for days 4-6. When *M. fructicola* was used without the booster formulation, rotting was at about 30% on day 4 and about 90% by day 6. But in the replicates using *M. fructicola* with the booster formulation, there was a significant positive affect on rotting for all days tested. In that case, rotting was reduced to under 20% on day 4, and less than 70% on day 6.

While the invention has been illustrated and described in detail in the drawings and foregoing description, the same is considered to be illustrative and not restrictive in character, it is understood that only the preferred embodiments have been shown and described and that all changes and modifications that come within the spirit of the invention are desired to be protected.

The invention claimed is:

1. A composition for improving the ability of an antagonistic microorganism to suppress or treat disease or decay in plants, comprising an antagonistic microorganism and a booster composition, wherein said booster composition comprises:
   a) 2 to 4 parts Kaolin clay;
   b) 1 to 1.5 parts yeast;
   c) 1 to 1.5 parts Yucca plant extract; and
   d) 1 to 1.5 parts calcium-source material.

2. A composition according to claim 1 wherein the composition comprises about 0.04 parts antagonistic microorganism per 1 part each of yeast, Yucca plant extract and calcium source material, by weight of the composition.

3. A composition according to claim 1 wherein the parts Kaolin clay, yeast, Yucca plant extract; and calcium-source material are dispersed in an aqueous preparation that includes between 1.5 and 10 pounds of Kaolin clay per 100 gallons of aqueous preparation.

4. A composition according to claim 1 wherein the calcium source material comprises a calcium salt.

5. A composition according to claim 4 wherein said calcium salt comprises calcium glucoheptonate, calcium chloride, calcium sulfate, or calcium carbonate.

6. A composition according to claim 4 wherein said calcium salt comprises calcium glucoheptonate.

7. A composition according to claim 1 wherein the antagostic microorganism comprises one or more beneficial bacteria.

8. A composition according to claim 1 wherein the antagonistic microorganism comprises one or more beneficial fungi.

9. A composition according to claim 8 wherein the one or more beneficial fungi comprises one or more beneficial yeasts.

10. A composition according to claim 8 wherein the one or more beneficial bacteria comprises one or more beneficial bacteria selected from the group consisting of: *Azotobactor chroococcum, Azobacter polymyxa, Azobacter vinleandii, Bacillus amyloliquefaciens, Bacillus azotoformans, Bacillus coagulans, Bacillus fluorescens, Baccillus licheniformis, Bacillus megaterium, Bacillus polymyxa, Bacillus pumilis, Bacillus sterotermophilis, Bacillus subtilis, Bacillus thuringiensis, Deinococcus erythromyxa, Paenibacillus azotofixans, Paenibacillus durum, Paenibaccillus gordonae, Paenbacillius polymyxa, Pseudomonas aureofaceans, Pseudomonas fluorescens, Pseudomonas monteilii, Streptomyces griseoviridis*, and *Streptomyces lydicus*.

11. A composition according to claim 8 wherein the one or more beneficial bacteria comprises one or more beneficial bacteria selected from the group consisting of: *Azotobactor chroococcum, Azobacter polymyxa, Bacillus amyloliquafacians, Bacillus azotofomrans, Bacillus coagulans, Baccillus licheniformis, Bacillus megaterium, Bacillus pumulis, Bacillus stearothermophilis, Bacillus subtilus, Bacillus thurengiensis, Deinococcus erythromyxa, Paenibaccillus durum, Paenibaccillus gordonae, Paenbacillius polymyxa, Pseudomonas aureofaceans*, and *Pseudomonas fluorescence*.

12. A composition according to claim 8 wherein the one or more beneficial fungi comprises *Monilinia fructicola*.

13. A composition according to claim 9 wherein the one or more beneficial yeasts comprises one or more beneficial yeasts selected from the group consisting of: *Candida* spp; *Cryptococcus* spp; *Pichia* spp; *Debaryomyces* spp; *Bulleromyces* spp; *Sporobolomyces* spp; *Rhodotorula* spp; *Aureobasidium* spp; *Issatchenkia* spp; *Zygosaccharomyces* spp; *Dekkera* spp; and *Hansenula* spp.

14. A composition according to claim 9 wherein the one or more beneficial yeasts comprises *Candida saitoana*.

15. A composition according to claim 1 wherein the composition comprises:
   a) about 3 parts Kaolin clay;
   b) about 1 part yeast;
   c) about 1 part Yucca plant extract; and
   d) about 1 part calcium-source material.

* * * * *